United States Patent [19]

Wallace

[11] 4,278,886
[45] Jul. 14, 1981

[54] IN-LINE ASSAY MONITOR FOR URANIUM HEXAFLUORIDE

[75] Inventor: Steven A. Wallace, Knoxville, Tenn.

[73] Assignee: The United States of America as represented by the United States Department of Energy, Washington, D.C.

[21] Appl. No.: 132,433

[22] Filed: Mar. 21, 1980

[51] Int. Cl.³ .............................. G01J 1/42; G01T 1/00
[52] U.S. Cl. .................................... 250/393; 250/394; 250/492 R
[58] Field of Search ............ 250/492 R, 432 R, 358 R, 250/393, 394, 395

[56] References Cited
U.S. PATENT DOCUMENTS

| 3,242,337 | 3/1966 | Mackenzie et al. | 250/393 |
| 3,376,200 | 4/1968 | Ward | 250/393 |
| 3,597,615 | 8/1971 | Dolenko et al. | 250/393 |

Primary Examiner—Bruce C. Anderson
Attorney, Agent, or Firm—David E. Breeden; Stephen D. Hamel; Richard G. Besha

[57] ABSTRACT

An in-line assay monitor for determining the content of uranium-235 in a uranium hexafluoride gas isotopic separation system is provided which removes the necessity of complete access to the operating parameters of the system for determining the uranium-235 content. The monitor is intended for uses such as safeguard applications to assure that weapons grade uranium is not being produced in an enrichment cascade. The method and monitor for carrying out the method involve cooling of a radiation pervious chamber connected in fluid communication with the selected point in the system to withdraw a specimen and solidify the specimen in the chamber. The specimen is irradiated by means of an ionizing radiation source of energy different from that of the 185 keV gamma emissions from the uranium-235 present in the specimen. Simultaneously, the gamma emissions from the uranium-235 of the specimen and the source emissions transmitted through the sample are counted and stored in a multiple channel analyzer. The uranium-235 content of the specimen is determined from the comparison of the accumulated 185 keV energy counts and the reference energy counts. The latter is used to measure the total uranium isotopic content of the specimen. The process eliminates the necessity of knowing the system operating conditions and yet obtains the necessary data without need for large scintillation crystals and sophisticated mechanical designs.

9 Claims, 1 Drawing Figure

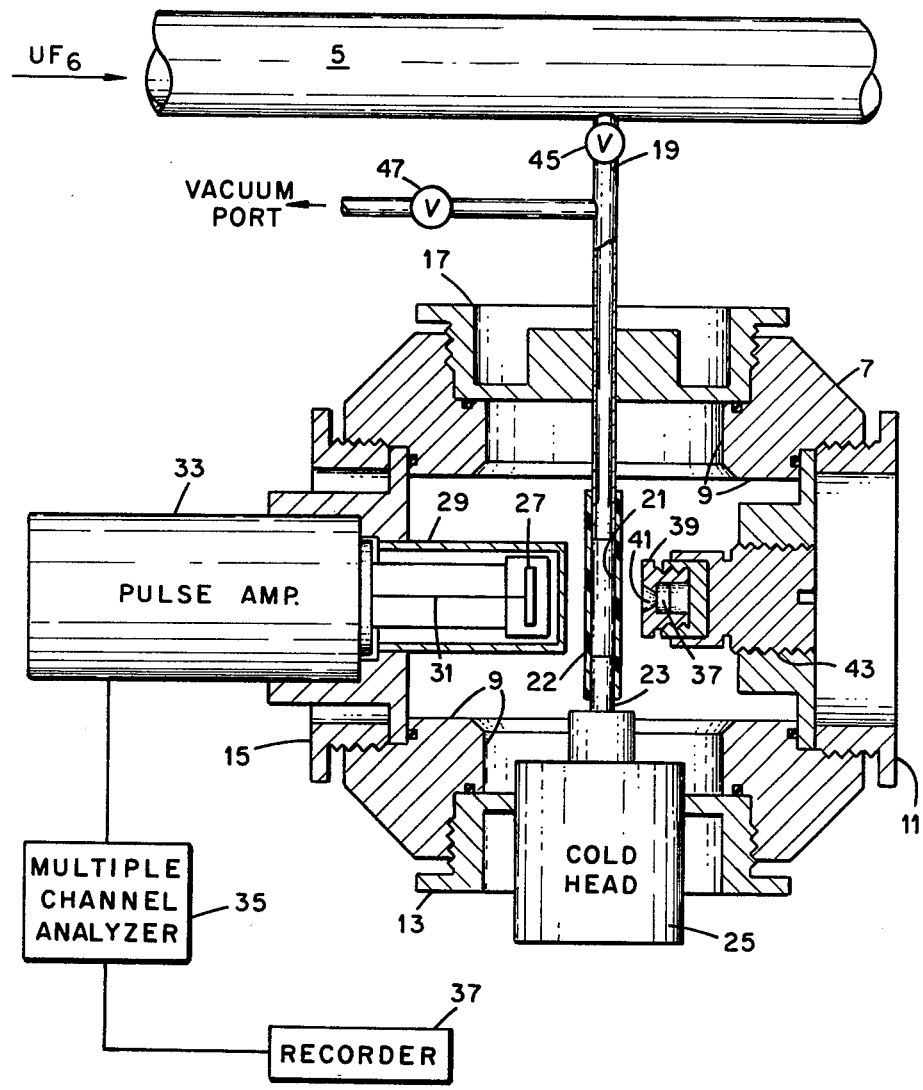

IN-LINE ASSAY MONITOR FOR URANIUM HEXAFLUORIDE

BACKGROUND OF THE INVENTION

This invention relates generally to assaying of isotopic gaseous separation systems and more particularly to a uranium isotope separation monitoring method and system for determining the uranium-235 ($^{235}$U) enrichment in a uranium separation process, wherein the uranium is in the form of uranium hexafluoride (UF$_6$) in the gaseous state, without the knowledge of the operating parameters of the gas system. This invention is a result of a contract with the U.S. Department of Energy.

In certain applications, such as safeguards inspection and monitoring of a uranium isotope separation plant wherein the uranium is in the form of UF$_6$ in the gaseous state, it is desirable to audit the $^{235}$U enrichment factor without access to the process plant operating parameters. While a safeguards inspection team could conduct a $^{235}$U audit more accurately by obtaining samples from various points in the process stream and isotopically analyzing them, permission to do this might not be granted; therefore, a method for determining the $^{235}$U enrichment of the UF$_6$ gas inside the process equipment from measurements made outside the equipment must be available. Particularly in the case of a centrifuge cascade, the UF$_6$ is circulated at subatmospheric pressure to maintain the UF$_6$ in the gaseous state at ambient temperatures. Because of the low pressure of the gas in the cascade piping and since in all locations the $^{238}$UF$_6$ isotope may comprise more than 95% of the gaseous mixture, only a few gamma rays of 185 keV energy are observed due to the decay of the $^{235}$UF$_6$ component per unit length of pipe over a particular area. To generate enough signal for a statistically valid measurement of the $^{235}$U content in the gas mixture would require large scintillation crystals with large shields of sophisticated design. Further, the pressure would need to be known in order to infer the total quantity of gas being observed.

Measurement of the $^{235}$U content, without knowledge of total UF$_6$ present or other system operating conditions, may be carried out by first obtaining a direct measurement of the 185 keV $^{235}$U gamma radiation in a section of pipe, measuring the gamma transmission to determine attenuation by the pipe and total UF$_6$ combined, making a correction for the attenuation by the pipe wall to provide an estimate of absorption due to UF$_6$ alone and calculation of total UF$_6$ in the pipe based on this attenuation effect. The ratio of $^{235}$U-to-total uranium would then be the necessary enrichment factor. The above procedure is a laborious process requiring elaborate new shielding designs and calibrations for every different pipe diameter. The received radiation from the $^{235}$U is strongly affected by the geometrical configuration and unfortunately is best determined by the laborious experimental mock-up method.

SUMMARY OF THE INVENTION

It is, therefore, an object of this invention to provide a method for measuring the assay of $^{235}$U in a uranium isotopic separation system wherein the uranium is in the form of UF$^6$ in the gaseous state without the knowledge of the gas density within the system.

Another object of this invention is to provide a method for measuring the assay of $^{235}$U in a gaseous uranium hexafluoride isotopic separation system in which the operating parameters of the system are unknown.

Further, it is an object of this invention to provide a monitor for carrying out the method of the above objects.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the method for measuring $^{235}$U assay of a uranium hexafluoride gas system of this invention may comprise: cooling a chamber which is continually connected in fluid communication with the UF$_6$ uranium isotope separation system, wherein the UF$_6$ is in the gaseous state to withdraw a specimen of the gas into the chamber and to solidify the gas in the chamber; irradiating the solid specimen with a radiation source which emits ionizing radiation of an energy different from that emitted by the spontaneous gamma ray emission from $^{235}$U present in the specimen, while simultaneously measuring the quantity of radiation emitted by the $^{235}$U present in the specimen and the quantity of source irradiation transmitted through the specimen. These quantitative radiation measurements are used to determine the fraction of $^{235}$U present in the specimen relative to the total uranium present in the specimen, thereby determining the $^{235}$U enrichment of the system.

In a further aspect of the present invention, a monitor is provided for measuring $^{235}$U content of a UF$_6$ process gas system wherein a radiation pervious chamber is connected in fluid communication with the system. Means is provided for selectively cooling the chamber to withdraw a specimen of gas from the system into the chamber and solidfy the specimen in the chamber. An ionizing radiation source is disposed to direct ionizing radiation of an energy substantially different from that emitted from the $^{235}$U of the system through the chamber and the solidified UF$_6$ within the chamber. A radiation detector is disposed to detect the emissions from the $^{235}$U component of the solid specimen and radiation from the source transmitted through the specimen. Means are provided for counting and separately recording the quantity of radiation detected from the $^{235}$U and that transmitted through the specimen from the source.

In accordance with the invention, safeguards measurements of the uranium enrichment in a UF$_6$ gaseous enrichment system may be obtained without the operator's knowledge of the density of the gas or other operating parameters of the system. This allows measurements to be made to determine whether or not weapons grade material is being produced in the separation system without disturbing the complex balance within the sparation system. Further, since the specimen is returned to the system simply by allowing the specimen to return to room temperature, the system may be modified to provide an automatic or remotely operated data-collection system without access to the process system per se.

BRIEF DESCRIPTION OF THE DRAWING

The accompanying drawing, which is incorporated in and forms a part of the specification, illustrates the present invention and, together with the description, serves to explain the principals of the invention. In the single FIGURE there is a schematic illustration of the preferred embodiment of a monitor in accordance with the subject invention wherein a small chamber is disposed within a housing. The chamber is in fluid communication with a $UF_6$ gas process line. A cold head is provided for cooling the chamber to collect and solidify a sample from the line and a radiation source is disposed to transmit ionizing radiation through the specimen into a detector which is connected to the recording system to separately record the quantity of irradiation from the $^{235}U$ in the sample and the source radiation transmission through the sample.

DETAILED DESCRIPTION OF THE INVENTION

Referring now to the drawing, there is shown an embodiment of the subject invention connected to a process line 5 of a uranium isotope separation system wherein the uranium is in the form of $UF_6$ in the gaseous state. The system is operated at subatmospheric pressure to maintain the $UF_6$ in the gaseous state at ambient temperature levels. The $UF_6$ gas mixture contains $^{235}U$ hexaflouride and $^{238}U$ hexaflouride as the primary components. However, it will be understood that there are other small quantities of gas of insignificant proportion in the gas mixture, but that the $UF_6$ gas is of primary interest and the component to be measured to obtain the enrichment factor of $^{235}U$ in the $^{235}UF_6$ gaseous state.

The monitor consists of a cube-shaped housing 7 shown here in cross section. This housing is evacuated to prevent extraneous heat loss into the cold finger and prevent frost formation. The housing has a plurality of cylindrical access openings which threadably receive accessory support plugs 11–17 each centrally aligned in the corresponding walls of the housing 7. Plug 17 has a central opening through which a specimen transport tube, connected in fluid communication with the system line 5 at one end, enters the housing and is terminated at the opposite end by a specimen chamber 21 sealably attached to the end of the tube 19 and located centrally of the housing 7. The specimen chamber 21 may comprise a short section of polyethylene tubing 22 sized to be slipped over the end of the specimen transport tube 19 to form a gas-tight seal. The chamber volume and thus the tube size is selected so that minimal $UF_6$ is extracted from the process stream while still acquiring sufficient material to allow an enrichment to be ascertained within a reasonable measuring interval. Typically, the chamber 21 has a nominal dimension of 0.475 cm diameter by 1.90 cm length.

The opposite end of the tube sealably engages a cold finger 23 of a commercially available cold head 25. The cold head 25 may be mounted in the accessory plug 13 in a conventional thermally insulated manner. The cold head 25 operating through the heat transfer of the cold finger 23 cools the chamber 21 to withdraw a sample of gas from the system line 5 into the specimen chamber and further desublimes the $UF_6$ gas from the system as a solid in the chamber. Alternatively, liquid nitrogen may be used to cool the chamber 21 to obtain the same result. However, the cold head is more convenient especially if the system is to be automated or remotely operated. A typical commercial cold head which may be used with the monitor is a Model No. 21 supplied by CTI-Cryogenics, Waltham, MA.

Disposed in close proximity to the wall of the chamber 21 is an energy-sensitive ionizing radiation detector 27 mounted within a detector housing assembly 29 which attaches centrally to and extends through the accessory plug 15. The detector 27 is electrically connected by means of a lead wire 31 to the input of a pulse amplifier 33, which may also be carried by the accessory plug 15 as shown.

The detector 27 may be of various types which generate an electrical pulse each time an ionizing radiation event is detected by the detector medium 27. Detectors, such as a liquid nitrogen cooled germanium detector, a room temperature sodium iodide crystal, or a cadmium telluride detector, may be used. The detector 27 generates pulses at a rate proportional to the quantity of $^{235}U$ in the sample chamber 21 and these specific energy (185 keV) pulses are counted in a separate channel of a multichannel analyzer 35.

A radiation source 37 mounted within a conventional shielded source holder 39 is disposed on the opposite side of the chamber 21 from the detector 27 and is selected to produce radiation of an energy different from the 185 keV energy pulses produced by the $^{235}U$ or the specimen within the chamber 21. For example, 60 keV energy from an americium-241 radiation source may be used. The source holder 39 is disposed so that the source 37 irradiates sample chamber 21 through the source holder aperture 41. This is accomplished by mounting the source holder 39 on the end of a threaded plug 43. The threaded plug 43 engages the accessory plug 11, as shown, which allows the source to be removed or adjusted closer or farther from the chamber 21.

The signal reaching the multichannel analyzer 35 due to the radioactive source, is decreased due to attenuation of the total quantity of solidified $UF_6$ present in the chamber 21. As a result, both the total quantity of $UF_6$ present and the partial fraction of the $^{235}U$ component may be determined from the specimen. When the monitor is calibrated, this measurement directly infers the enrichment factor of the process gas in the line 5.

These measurements are made by counting both the gamma rays spontaneously generated by the decay of the $^{235}U$ in the chamber 21 and the extent of attenuation of the source 37 radiation through the specimen for a predetermined period of time (typically not exceeding 10 hours) to obtain a statistically accurate pulse count. The reason for the long counting period is due to the fact that in certain portions of an enrichment system the $^{235}U$ component of the specimen is relatively small. The accumulative counts may be recorded in various manners such as a magnetic tape recorder 37 connected to store the count spectra in the separate channels of the analyzer 35.

In order to calibrate the instrument standard $UF_6$ gas samples of 0.3, 0.7 and 2% enriched $^{235}UF_6$ may be used. A standard bottle containing mass spectrographically analyzed $UF_6$ is attached to the monitor. The same procedure, i.e., cooling to freeze a sample specimen, taking a spectra, warming the sample to evacuate the chamber 21, is done at different assays. This establishes the empirical calibration for the size chamber 21 selected.

In accordance with the method of the invention, the chamber 21 is cooled to a temperature which causes a gas sample from the line 5 to enter the chamber through the access tube 19. Once the collected specimen is solidified, the temperature is maintained to keep the specimen in the solid state during the period of time the radiation measurements are made. After the measuring period is completed the cold head 25 may be turned off allowing the specimen in the chamber 21 to warm up to room temperature under which conditions the specimen returns to the gaseous state and re-enters the process gas stream in the line 5.

Standard engineering practice introduces two additional valves (45 and 47) to the monitoring system. An isolation valve 45 allowing removal or attachment of the monitoring system is attached to the process pipe 5. An evacuation valve 47 allowing the air in the line 19 and chamber 21 to be exhausted prior to opening the isolation valve 45 is present. This valve 47 is opened, the line 19 is evacuated and the valve is closed. It remains closed and is not required again.

The above-described procedure uses only small quantities of $UF_6$ in making a $^{235}U$ assay determination. Further, no gas is extracted from the system, since, upon warmup, the specimen returns to the system. The method may be made cyclical and with an appropriate refrigeration system under computer control of the data collection and recording system no active operator intervention is required. A running calibration is available since readings of the radiation source transmission through the chamber taken between samples allows any residual deposits affecting background to be compensated for.

With tamper-proofing, the subject apparatus can be used as a continuous on-stream instrument for measuring $^{235}U$ content in a gas centrifuge or diffusion cascade as a safeguard against reconfiguration of an enrichment facility to produce weapons grade material.

The foregoing description of preferred embodiments of the invention has been presented for purposes of illustration and description. It is not intended to be exhaustive or to limit the invention to the precise form disclosed, and obviously many modifications and variations are possible in light of the above teaching. The specific embodiment of the monitor was chosen and described in order to best explain the principals of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring the uranium-235 enrichment of a uranium hexafluoride gas system independent of the density of the gas within the system, comprising the steps of:
    cooling a radiation pervious chamber connected in fluid communication with said system to withdraw a specimen of the gas from said system into said chamber and to solidify said gas in said chamber;
    irradiating said solidified specimen with a radiation source which emits ionizing radiation of an energy different from that emitted by the spontaneous gamma ray emission from uranium-235 present in said specimen;
    measuring the quantity of radiation emitted by said specimen and the quantity of radiation transmitted through said specimen; and
    determining the fraction of uranium-235 present in said specimen relative to the total uranium present in said specimen from the respective radiation quantity measurements as a measure of the uranium-235 enrichment factor of the system.

2. The method as set forth in claim 1 further including the step of returning said specimen to said system in the gaseous state.

3. The method as set forth in claim 1 wherein said irradiating and measuring steps are performed simultaneously.

4. The method as set forth in claim 3 wherein said radiation source is americium-241.

5. A device for measuring the uranium-235 content of a uranium hexafluoride process gas system, comprising:
    an ionizing radiation previous member forming a specimen chamber connected in fluid communication with said system;
    cooling means for selectively cooling said chamber to withdraw a specimen of gas from said gas system into said chamber and solidify said specimen in said chamber;
    an ionizing radiation source disposed to direct ionizing radiation of an energy substantially different from that emitted from said uranium-235 of said gas system through said chamber; and
    means for detecting and recording ionizing radiation from the uranium-235 of said solidified specimen and source radiation transmitted through said sample from said ionizing radiation source.

6. The device of claim 5 wherein said means for detecting and recording includes an energy-sensitive ionizing radiation detector disposed adjacent said chamber on the side opposite said one side of said chamber and means for counting and separately recording ionizing radiation events from said uranium-235 and that transmitted through said specimen from said source.

7. The device of claim 5 wherein said ionizing radiation pervious member includes a cylindrical tube section forming said chamber and having a preselected volume for collecting a sufficient amount of said specimen to determine the U-235 component thereof at predetermined counting intervals of not greater than 10 hours and further including a specimen transfer tube connected between said process gas system and said cylindrical section tube.

8. The device of claim 7 further including housing means for enclosing and proving a vacuum environment for said specimen chamber, said radiation source and said detector.

9. The device of claim 8 wherein said cooling means includes a cold head connected in thermal communication with said chamber.

* * * * *